United States Patent
Mahesh et al.

(10) Patent No.: US 8,151,188 B2
(45) Date of Patent: Apr. 3, 2012

(54) INTELLIGENT USER INTERFACE USING ON-SCREEN FORCE FEEDBACK AND METHOD OF USE

(75) Inventors: Prakash Mahesh, Hoffman Estates, IL (US); Timothy Kenney, Burlington, VT (US); James Whitfill, Phoenix, AZ (US)

(73) Assignee: General Electric Company, Schenectady, NY (US)

( * ) Notice: Subject to any disclaimer, the term of this patent is extended or adjusted under 35 U.S.C. 154(b) by 644 days.

(21) Appl. No.: 12/178,258

(22) Filed: Jul. 23, 2008

(65) Prior Publication Data

US 2010/0023857 A1 Jan. 28, 2010

(51) Int. Cl.
*G06F 3/00* (2006.01)
*G06F 3/048* (2006.01)

(52) U.S. Cl. .......................... 715/701; 715/702; 715/856

(58) Field of Classification Search .................. 715/834, 715/701–702, 856; 600/437
See application file for complete search history.

(56) References Cited

U.S. PATENT DOCUMENTS

| | | |
|---|---|---|
| 5,500,935 A | 3/1996 | Moran et al. |
| 5,643,087 A | 7/1997 | Marcus et al. |
| 6,219,032 B1 | 4/2001 | Rosenberg et al. |
| 6,243,078 B1 * | 6/2001 | Rosenberg ..................... 345/161 |
| 6,549,219 B2 | 4/2003 | Selker |
| 2002/0054019 A1 * | 5/2002 | Rosenberg et al. ........... 345/157 |
| 2009/0043195 A1 * | 2/2009 | Poland .......................... 600/437 |

* cited by examiner

*Primary Examiner* — Tuyetlien Tran
*Assistant Examiner* — Truc Chuong
(74) *Attorney, Agent, or Firm* — Hanley, Flight & Zimmerman, LLC

(57) ABSTRACT

Certain embodiments of the present invention provide methods and systems combining user interface features with force feedback techniques in clinical applications. Certain embodiments provide a user interface providing clinical software tools and information access for a picture archiving and communication system. The user interface includes a plurality of regions displayed to represent selectable functionality for an associated plurality of clinical software tools and information. The user interface also includes a cursor movable by a user to select one of the plurality of regions. The user interface further includes a processor configured to determine a location and pattern of movement of the cursor and provide force feedback to the user based on the location and pattern of movement of the cursor to provide a non-visual indication to the user of the location and pattern of movement of the cursor.

15 Claims, 5 Drawing Sheets

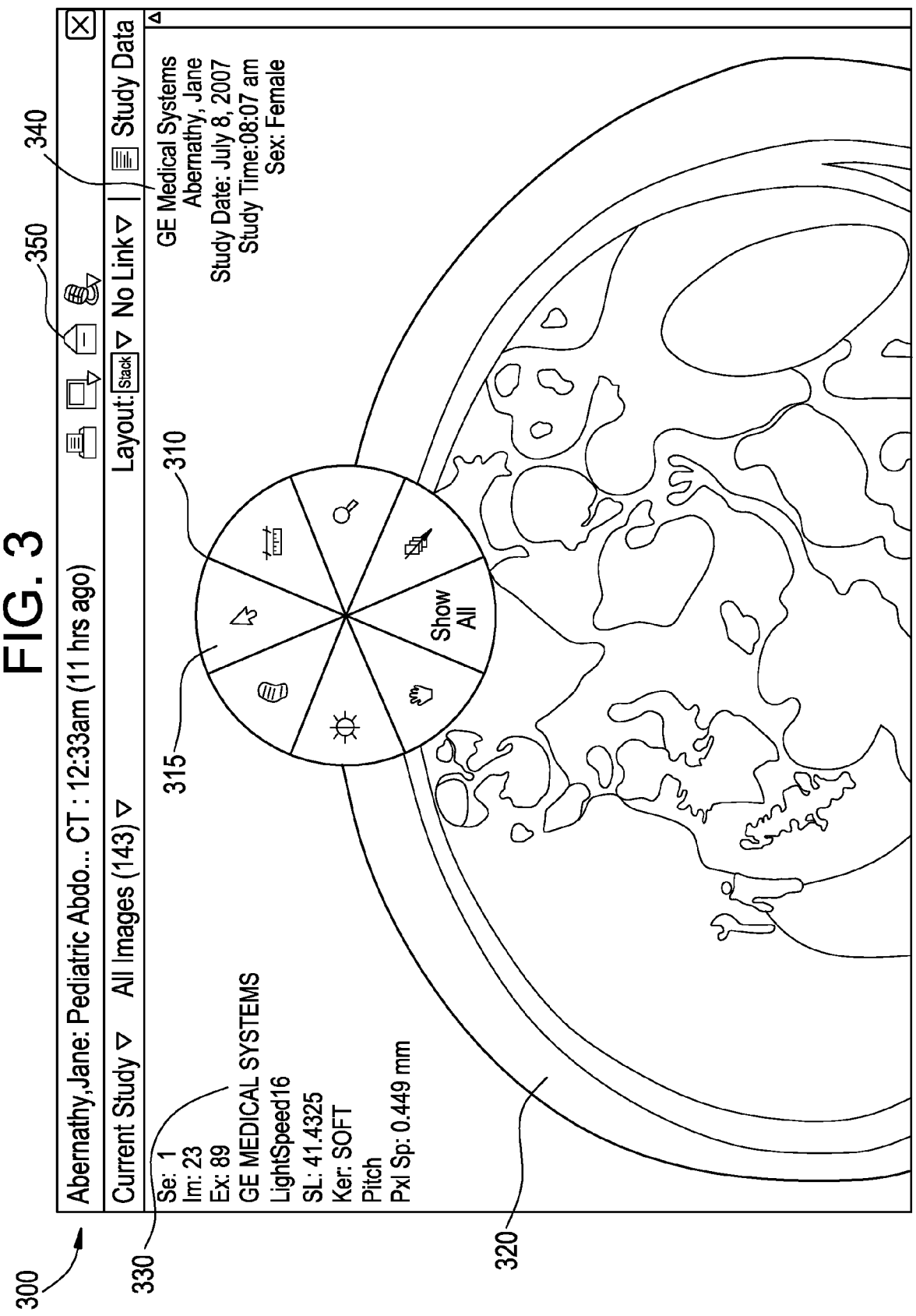

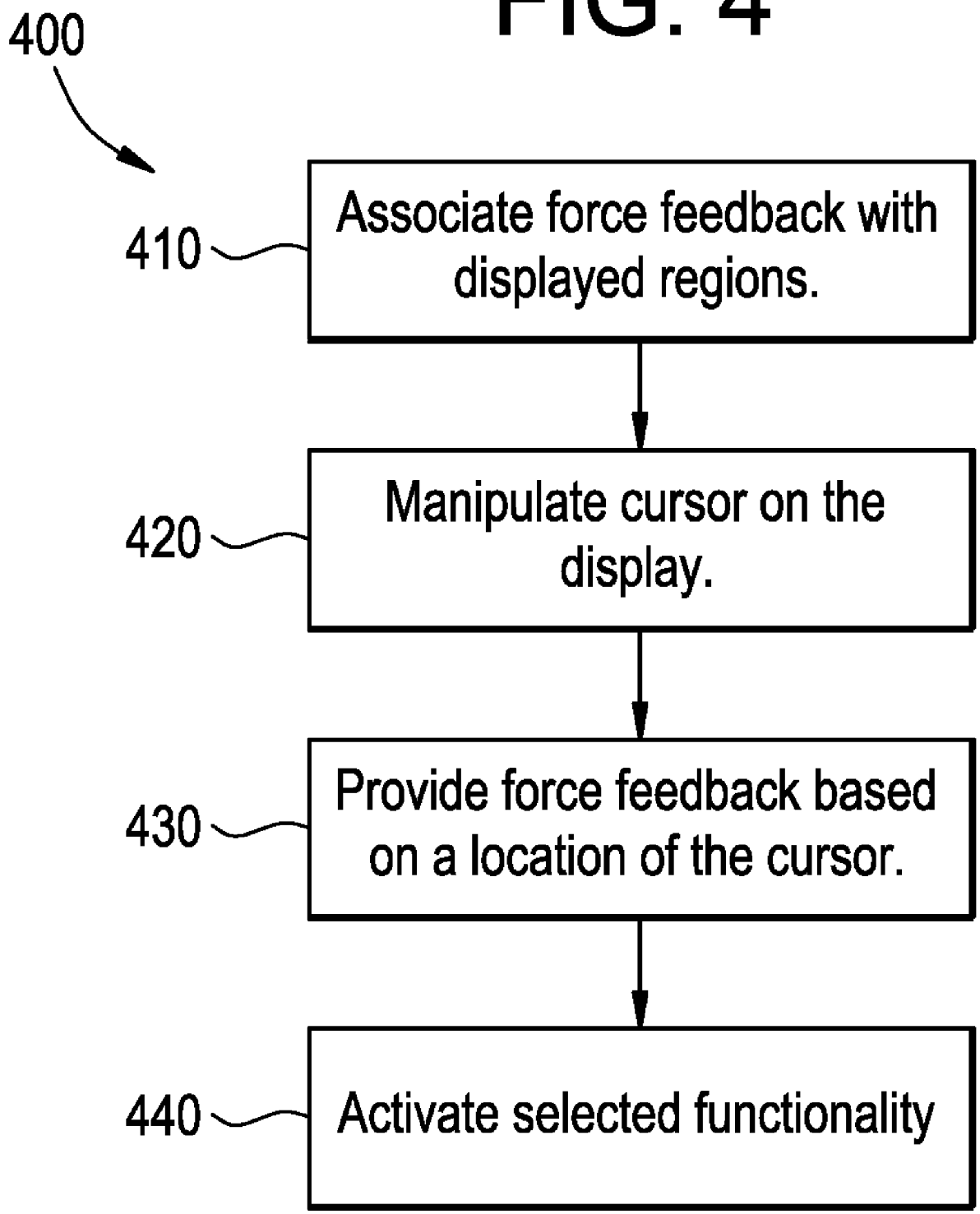

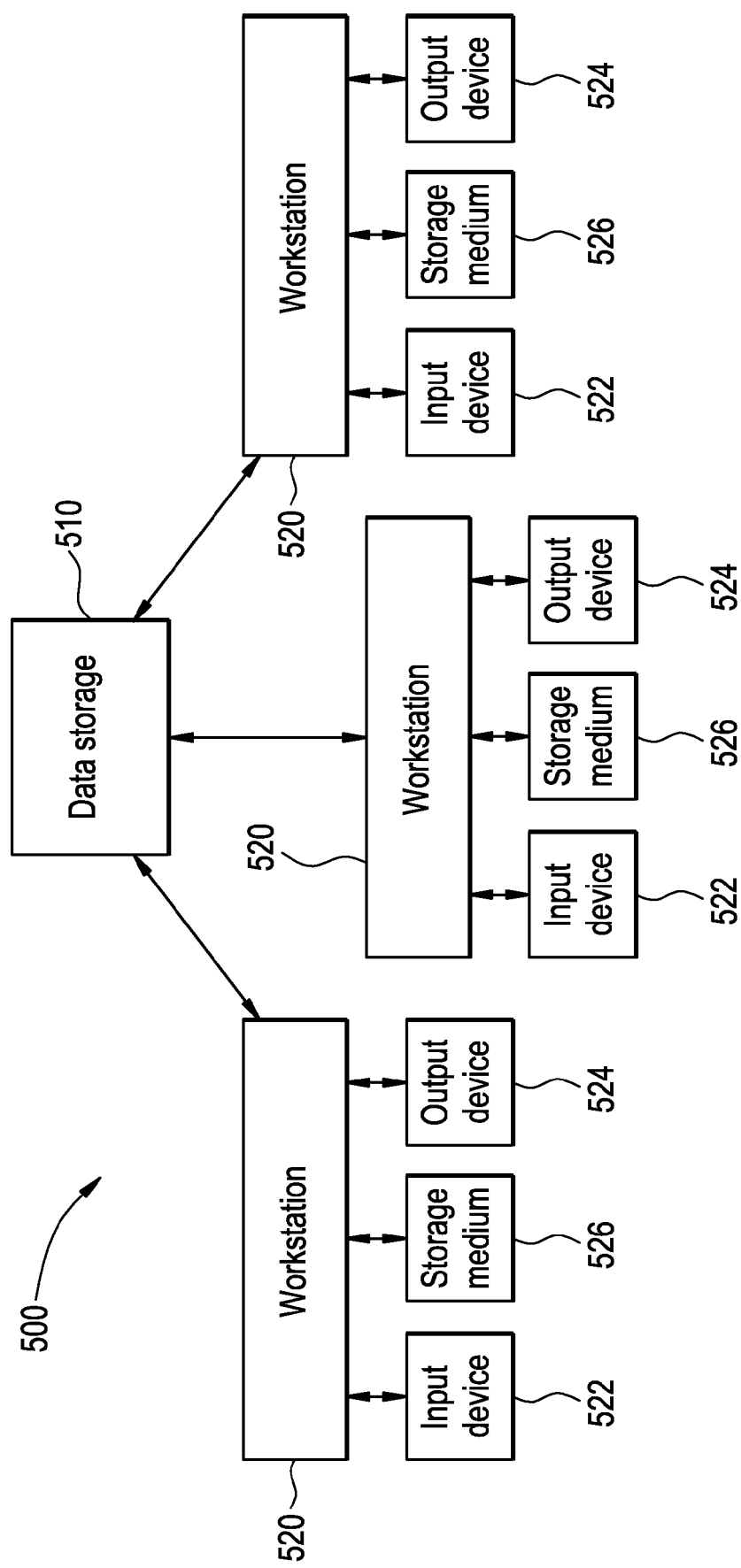

INTELLIGENT USER INTERFACE USING ON-SCREEN FORCE FEEDBACK AND METHOD OF USE

BACKGROUND OF THE INVENTION

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during and/or after surgery, medical personnel may access patient information, such as images of a patient's anatomy, that are stored in a medical information system. Radiologist and/or other clinicians may review stored images and/or other information, for example.

Using a PACS and/or other workstation, a clinician, such as a radiologist, may perform a variety of activities, such as an image reading, to facilitate a clinical workflow. A reading, such as a radiology or cardiology procedure reading, is a process of a healthcare practitioner, such as a radiologist or a cardiologist, viewing digital images of a patient. The practitioner performs a diagnosis based on a content of the diagnostic images and reports on results electronically (e.g., using dictation or otherwise) or on paper. The practitioner, such as a radiologist or cardiologist, typically uses other tools to perform diagnosis. Some examples of other tools are prior and related prior (historical) exams and their results, laboratory exams (such as blood work), allergies, pathology results, medication, alerts, document images, and other tools. For example, a radiologist or cardiologist typically looks into other systems such as laboratory information, electronic medical records, and healthcare information when reading examination results.

Currently, PACS systems display a full array of available tools redundantly in a PACS imaging window. As illustrated, for example, in FIG. 1, tool bars and functionality buttons clutter the screen. In the radiology industry, for example, redundant tools for radiology reading and other functions are positioned all over a workstation's imaging window, creating unnecessary clutter. As shown in FIG. 1, for example, a right click tool menu requires a radiologist to extensively navigate to select an appropriate imaging tool. Positioning of these tools in the viewing window forces the radiologist to search for a particular tool which, due at least in part to the complexity of the imaging screens, can cause inefficiencies in the reading workflow.

Current tools also force radiologists to select tools from locations on the imaging screens that require unnatural hand/mouse movements. Studies suggest that tool selection can account for up to 10% of the time taken for the diagnostic interpretation process.

Most user interface designs in the last twenty years have made some basic assumptions such as requiring the presence and use of a keyboard, a mouse, and a CRT/LCD monitor. Current user interface design is also forced to function with respect to some early design choices, such as a QWERTY keyboard, since users are familiar with those designs, and it is difficult to change user habits. Additionally, in an imaging system, using a conventional menu system takes a user's focus away from his or her tasks. Even if a user has used the same menu system many times, the user will still need to look at the menu to make a selection. Such a user interface design is not intuitive and takes substantial effort to navigate.

BRIEF SUMMARY OF THE INVENTION

Certain embodiments of the present invention provide methods and systems combining user interface features with force feedback techniques in clinical applications.

Certain embodiments provide a user interface providing clinical software tools and information access for a picture archiving and communication system. The user interface includes a plurality of regions displayed to represent selectable functionality for an associated plurality of clinical software tools and information. The user interface also includes a cursor movable by a user to select one of the plurality of regions. The user interface further includes a processor configured to determine a location and pattern of movement of the cursor and provide force feedback to the user based on the location and pattern of movement of the cursor to provide a non-visual indication to the user of the location and pattern of movement of the cursor.

Certain embodiments provide a computer-readable storage medium including a set of instructions for execution on a processing device and associated processing logic. The set of instructions include a user interface routine displaying a plurality of regions representing selectable functionality for an associated plurality of clinical software tools and information. The set of instructions also include a processing routine configured to determine a location and pattern of movement of a cursor movable by a user to select one of the plurality of regions and provide force feedback to the user based on the location and pattern of movement of the cursor to provide a non-visual indication to the user of the location and pattern of movement of the cursor.

Certain embodiments provide a method for providing force feedback to a user in conjunction with a user interface or application display in a clinical system. The method includes associating a degree of force feedback with a region of a display and a boundary of the region. The method also includes tracking manipulation of a cursor with respect to the region on the display. The method further includes providing the force feedback to a user when the cursor enters and leaves the region.

BRIEF DESCRIPTION OF SEVERAL VIEWS OF THE DRAWINGS

FIG. 3 depicts an interface providing user-configurability of a pie menu in accordance with an embodiment of the present invention.

FIG. 4 shows a flow diagram for a method for providing force feedback to a user in a clinical user interface according to an embodiment of the present invention.

FIG. 5 illustrates a system for clinical data storage and retrieval in accordance with an embodiment of the present invention.

Figure 1:
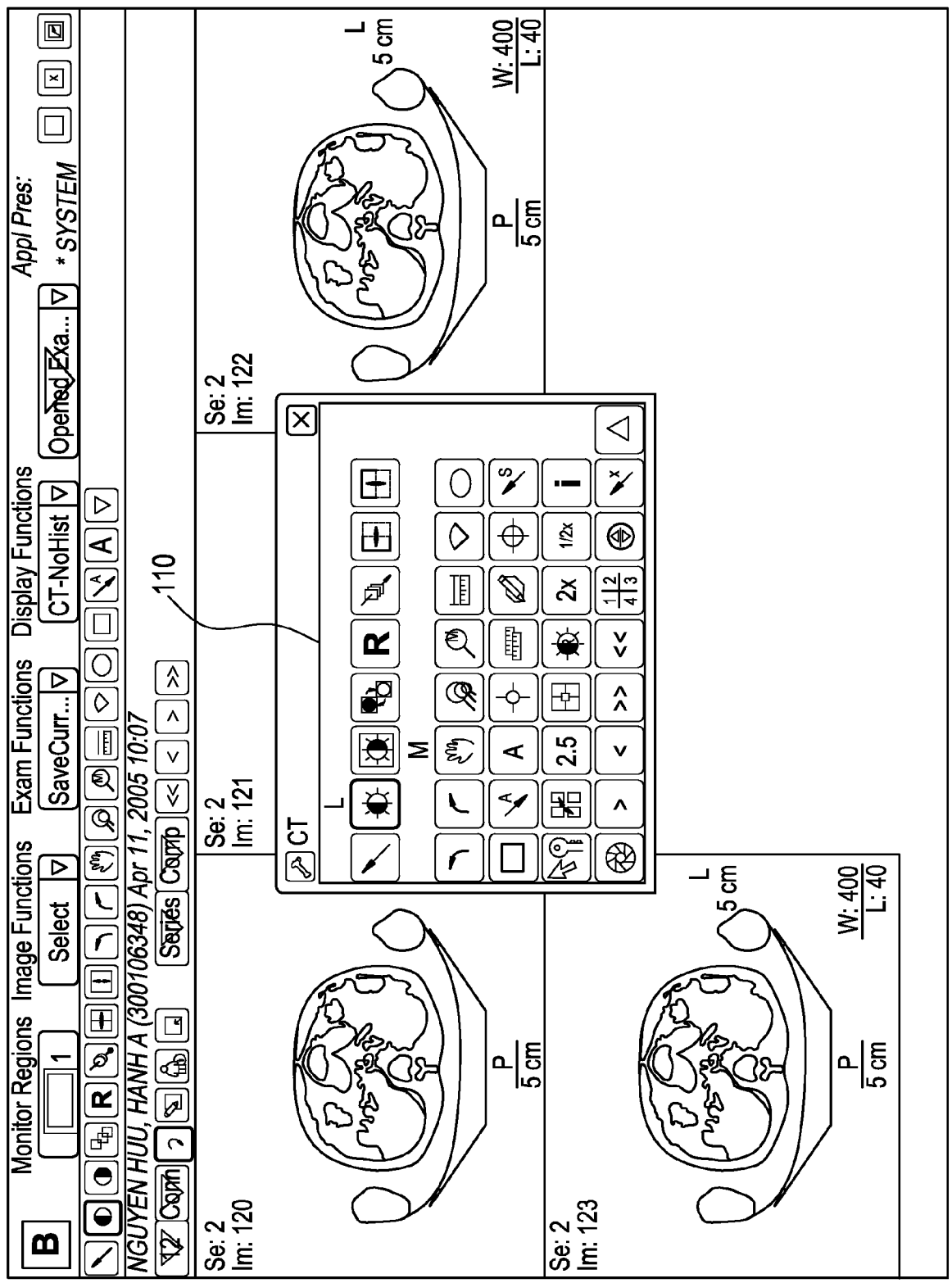
FIG. 1 shows a user interface cluttered with tool bars and functionality buttons.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

As a user reviews images and/or other clinical data, the user is provided with a user interface including image data (e.g., digital images) and tools to aid the user in review and diagnosis. Tools can include prior and related prior (historical) exams and results, laboratory exams (such as blood work), allergies, pathology results, medication, alerts, document images, and other tools. For example, a radiologist or cardiologist typically looks into other systems such as laboratory information, electronic medical records, and healthcare information when reading examination results.

Certain embodiments provide a combination of user interface features and techniques. For example, on-screen navigation is combined with force feedback to provide a user with feedback regarding which item(s) a user can select via the interface and which item(s) the user cannot select. Certain embodiments provide touch/on-screen controls with force feedback and a user interface design that uses such feedback to help users intuitively select functions without having to see the controls.

Figure 2:
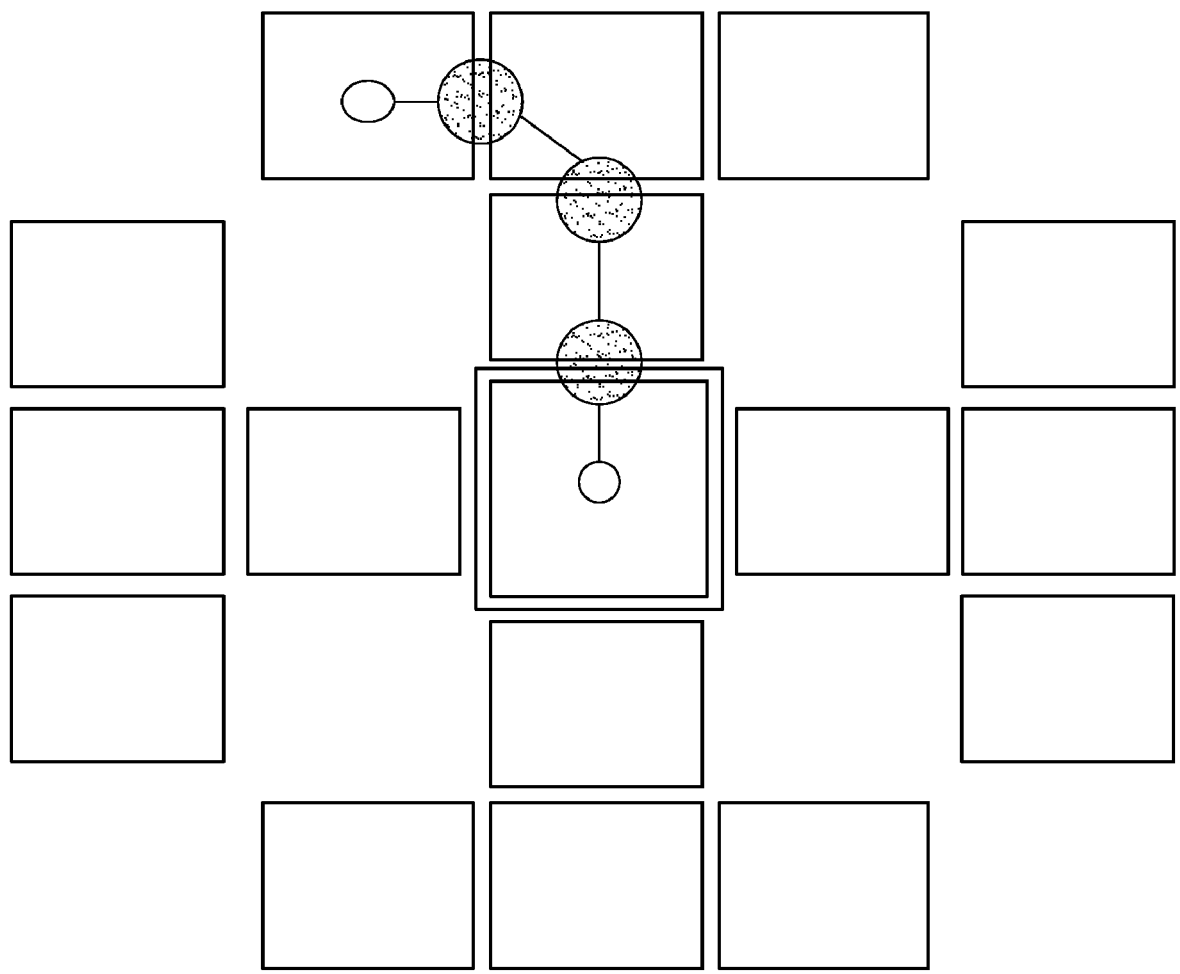
FIG. 2 illustrates an integration of a force feedback mechanism into a user interface display in accordance with an embodiment of the present invention.

As shown in FIG. 2, integration of a force feedback mechanism into a user interface display provides improved navigability and usability for a healthcare information system, such as a PACS, RIS, and/or other information system.

Graphical user interfaces typically require users to carefully move and position a user-controlled graphical object, such as a cursor or pointer, across a screen and onto other displayed graphical objects or predefined regions on a computer screen. Such manual tasks can be described as "targeting" activities where a user physically manipulates a mouse, joystick, or other interface device in order to command the cursor to a desired location or displayed object, known as a "target" herein. Targets can include, for example, icons for executing application programs and manipulating files; windows for displaying icons and other information; pull-down menus for selecting particular functions of the operating system or an application program; buttons for selecting presented options; and scroll bars or "sliders" for scrolling information in windows. Examples of targeting tasks include positioning a cursor on a graphical icon, selecting and pressing a graphical representation of a button, choosing among numerous items within a graphical representation of a pull-down menu, setting a continuous analog value from a provided range of values by positioning an indicator within a graphical representation of a scroll bar, selecting a region of text by highlighting a region using the cursor, as well as a number of other common windows-based and text-based metaphors.

Sensors determine a position, motion, and/or other characteristics of an object, such as a cursor, from the interface device, such as a mouse, trackball, thumbwheel, touchscreen, button, dial, knob, switch, stylus, joystick, wheel, band grip, medical instrument (e.g., laparoscope, catheter, etc.), and/or other mechanism, along one or more degrees of freedom and provide signals to a microprocessor associated with the computer system (such as a PACS workstation) including information representative of those characteristics. In certain embodiments, a sensor is provided for each degree of freedom along which the cursor can be moved. The user can manipulate and move the object along provided degrees of freedom to interface with a host application program the user is viewing on a display screen. Alternatively, a single compound sensor can be used to sense position or movement in multiple degrees of freedom. An example of sensors suitable for several embodiments described herein are digital optical encoders, which sense the change in position of an object about a rotational axis and provide digital signals indicative of the change in position. Linear optical encoders similarly sense the change in position of an object along a linear degree of freedom, and can produce signals in response to movement of a linear shaft in a linear degree of freedom. Either relative or absolute sensors can be used, for example. In certain embodiments, one or more analog sensors may be used in place of one or more digital sensors. An analog to digital converter (ADC) can convert the analog signal to a digital signal that is received and interpreted by a microprocessor.

Position value signals can be used by a microprocessor to update a user interface and/or a particular application program and sends force control signals as appropriate. For example, if the user moves the mouse cursor from a boundary of one icon on the user interface to another icon boundary, the position change and location of the cursor results in force feedback provided to the user. Other interface mechanisms can also be used to provide appropriate position and/or feedback signals.

The user interface with force feedback allows the position of cursor or other indicator generated in correspondence to movement of a device mouse, stylus, and/or other input device to be tracked and provides force feedback to the device using sensors and actuators, for example. One or more actuators and/or other transducer or motor transmit forces to the device in one or more directions along one or more degrees of freedom in response to signals received from a processor. In certain embodiments, an actuator is provided for each degree of freedom along which forces are desired to be transmitted. Actuators can include active and/or passive actuators.

Active actuators can include, for example, linear current control motors, stepper motors, and other types of actuators that transmit a force to move an object. Passive actuators can also be used for actuators.

An actuator interface can be optionally connected between the actuators and a microprocessor. The interface converts signals from the microprocessor into signals appropriate to drive the actuator(s). The interface can include power amplifiers, switches, digital to analog controllers (DACs), and other components, for example. In alternate embodiments, interface 38 circuitry can be provided within the microprocessor or actuator(s).

In operation, a user interface application and/or other application program such as an image review application is executed. Images, for example, can be displayed for a user and other feedback, such as audio feedback, can also be provided. A user can manipulate a cursor or other indicator using an input device, such as a computer mouse, trackball, touchscreen, stylus, etc., to view, select, and/or execute functionality via the interface/application. Such cursor movement is tracked by one or more sensors, such as motion/positional sensors incorporated into the input device and/or software tracking cursor position on a display. In certain embodiments, eye/gaze tracking may be used to track control cursor movement as well. In certain embodiments, tracking information can include rate of movement as well as position information (e.g., relative and/or coordinate-based positional data) in one or more degrees of freedom. In addition, data received from other input devices, such ash signals indicating a button push or item click on the interface, can also be received as tracking information. Further, tracking information can include a history or series of values such as a series of position values used to calculate a velocity of cursor movement.

Based on the position/tracking information, the user interface or application program can be updated based on cursor movement and/or object selection by the user. Additionally, a processor can determine, based on the position/tracking information, whether force feedback should be applied to the user via the input device and/or related component.

In certain embodiments, force feedback commands may vary depending upon one or more factors such as application, user input, cursor location, and the like. A force feedback command instructs an actuator or other such device to output a force of a particular magnitude. Force feedback commands can also designate a direction of force if an actuator can apply force in a selected direction, for example. A type or amount of force can be determined using user interface or application events, timing information, location information, velocity and/or acceleration of a cursor, button or other control activation, etc.

In certain embodiments, locations can be configured as target for force feedback. For example, a graphical object such as a menu item, button, icon, window, etc., on a display can be configured as targets to provide force feedback to a user. In certain embodiments, the target can be of a different size and/or shape than its associated graphical object. For example, a target perimeter can lie inside and/or outside a perimeter of the graphical object displayed on the screen.

Certain embodiments apply a variety of forces to a user control. Additionally, different forces can be applied to different areas of a graphical object on display. For example, a zero force (no force), a spring or damping force, and/or a texture force such as a groove and/or divot force, can be applied.

As an example, a texture or damping force feedback can be applied to alert the user that the cursor is positioned within a certain region on the screen. In certain embodiments, a damping force may be applied to help keep the cursor within a certain area of display. In certain embodiments, different regions on a display can provide differing force feedback to help the user distinguish between regions based at least in part on the feedback. In certain embodiments, boundaries between regions can be made apparent to the user through barrier force feedback. Barrier forces can be applied to provide an indication of the cursor passing from one target area to another and/or can be applied to create resistance for a user moving the cursor from one area to another, for example.

Thus, a variety of forces can be applied to a user device based on location of a cursor on a display. For example, a computer or other processor determines the location of the cursor on the screen and trigger software and hardware that provides the force feedback to the user device manipulating the cursor (e.g., a mousing device). Force feedback may be provided in conjunction with a graphical user interface to help the user navigate the interface and select items/locations on the interface display. Force feedback provides attraction forces, damping forces, and boundary or texture forces to improve user coordination without demanding a large amount of the user's attention in navigating.

In certain embodiments, as a user clicks once and moves the mouse up, the user feels when the mouse cursor crosses a line between menu items or options through force feedback applied to the mouse. As an example, one click of the mouse button activates the force feedback feature to provide boundaries and/or texture to blocks, lines, pie menu pieces and/or other regions of the display. The user can then "feel" the location with the mouse by pushing up and over. A second click of the mouse executes the selected function (e.g., a menu button over which the cursor is now positioned).

As shown in FIG. 2, such a force feedback interface design can be used to invoke up to 17 functions.

Thus, certain embodiments provide a technical effect of generating force feedback in conjunction with regions of a user interface or application. Certain embodiments provide a technical effect of enabling a user not to be seeing the menu as the user is trying to execute a command. That is, a user does not have to be diverted from his or her primary task to focus on the menu and select an option. The user without seeing will know which tool or command is selected using the force feedback.

Certain embodiments may be used in conjunction with a circular tree or pie menu allowing a user to select one or more of about 16-17 functions, for example, with a single click and touching. For example, a user clicking once as the mouse is moved up can feel the boundary line being crossed. Moving up twice and over one, for example, allows the user to define that region. One click activates the boundaries to allow the user to feel the cursor location. The second click executes a command/function.

In certain embodiments, cross a line or boundary into a menu sector can expand that sector and provide more options for selection within.

In certain embodiments, a display can be a touch screen providing force feedback (e.g., a Braille user interface) directly to a user's finger based on a region of the display touched.

In certain embodiments, depending upon the force applied, different menus are retrieved and activated/displayed for the user.

Certain embodiments help improve the speed at which doctors can execute their tasks. In Radiology, for example, one of the common complaints is the time and clicks it takes for a radiologist to get his or her job done. With this design, radiologists can do their diagnostic work much faster, with less intrusion, helping them in quality and quantity.

Certain embodiments may be used in conjunction with software based tools and associated systems and methods that allow users of a PACS system or related healthcare software application to easily select frequently-used tools with minimal searching on a user interface. Certain embodiments help to reduce redundant clutter on an image viewing screen, as welling as helping to reduce repetitive hand movements and helping to reduce a diagnostic interpretation process.

For example, a circular, pie-shaped menu can be provided that, upon activation, presents certain software tools to a user. For example, upon a right-click of a button, ball, wheel, switch and/or other action of a mousing device, the pie-shaped tool presents seven context sensitive software tools that include pan, zoom, window/level, cine, etc.

In certain embodiments, users are able to either activate a selected tool in a variety of ways. For example, a user may immediately click on his or her choice of tool to activate the tool from the menu. As another example, a user may mouse-down, drag and release the mouse button in an area of a selected tool to activate the tool from the menu. As another example, a user may use the mouse to click on the pie wedge at the six o'clock position to bring up a full set of tools from which to choose.

Certain embodiments allow PACS users to customize their preferred tools for each modality type (i.e., CT, MR, US, etc.) and also have an ability to quickly access the full set of tools available. To configure the pie menu for modality-specific tools, a user can open a particular modality type. Then, by clicking on or otherwise selecting the full array of tools, the user can drag and drop the preferred tools onto pie wedges. The user may select pie wedge locations for different tools according to a number of criteria including ease of use, frequency of use, etc.

In certain embodiments, in addition to the pie-shaped menu, complementary tools and functions associated with a selected tool may automatically populate on a tool bar, which could be positioned on the screen at the user's discretion. For example, when a selection arrow tool is enabled, an associated tool bar populates with related buttons and/or functions including select all, hide, show all, mark as significant, scout, reject, etc. Users can quickly select his or her tool from the pie menu and then quickly click to affect or leverage a related function.

Thus, certain embodiments provide a context sensitive pie menu including tools appropriate and/or customized for the particular context in which a PACS application is operating. Certain embodiments provide an associated tool ribbon or bar for the pie menu wedge items. Certain embodiments allow a user to customize the pie menu and tool ribbon or bar according to his or her applications and/or other preferences. Certain embodiments allow a user to access additional tools and/or access complimentary tools via the ribbon or bar.

The pie menu allows quick and easy access to, for example, the most frequently used tools. In other embodiments, the pie menu allows quick and easy access to the most recently used tools. The pie menu tool also affords an ability to drag and release an item in a gestural way that would allow for users to easily gesture to locations rather than having to look and choose particular tools on the screen. Thus, distractions, diversion of attention, and unnecessary computer interaction may be reduced.

An ability to drag and drop tools into the pie menu helps facilitate customization by a user. Context specific tools for each modality type help enable users to customize their menus for each specific modality rather than having to reconfigure the menu each time a modality is brought up.

Thus, a user interface including a pie menu and associated tool bar or ribbon may help eliminate redundant clutter on a viewing screen, allowing radiologists and clinicians to better focus on image information being displayed.

The new toolset helps improve or optimize the process of tool selection, which ultimately helps improve the diagnostic interpretation process.

In certain embodiments, in addition to allowing a user to customize a modality and context-sensitive tool menu using drag and drop functionality, the interface allows tool parameters and associated functions related to a specific tool to be accessed and customized by a user as well.

FIG. 3 illustrates an image viewing user interface 300 according to an embodiment of the present invention. The interface 300 includes, among other things, a pie menu tool 310, an image 320, image information 330, study information 340, and a tool ribbon 350. As depicted in FIG. 3, seven of the eight pie menu wedges 315 can be customized by a user to represent and trigger frequently accessed tools from a particular context or modality. In the example of FIG. 3, the eighth pie menu wedge 315 at the six o'clock position allows the user to bring up a full array of available tools in an organized fashion. In other embodiments not shown, the "show all" pie wedge may be positioned in another location on the menu tool 310. From the full tool windows, users have an ability to select their preferred tools and also drag and drop their favorite modality specific tools into the pie wedges 315 using a pointer, such as a mousing device and/or other instrument controlling an on-screen cursor, to setup their default favorites for a particular modality.

In certain embodiments, as an example, eight segments or wedges are provided for selectable tools. In other embodiments, an alternate number of wedges, such as segments corresponding to compass points north, south, east, and west, may be used. In certain embodiments, a user may configure a number of pie menu segments available for tool selection.

In certain embodiments, pie wedges can adjust based on usage data and can reorganize. In certain embodiments, pie wedges remain static to help facilitate repetitive and intuitive pie wedge selection based on user muscle memory. For example, a user's brain associates a cine tool with an up and right movement to select the cine tool so that the user does not have to focus on the pie menu to select the tool and can instead keep his or her focus on an image being reviewed.

FIG. 4 shows a flow diagram for a method 400 for providing force feedback to a user in a clinical user interface according to an embodiment of the present invention. At step 410, a force feedback is associated with a region of a displayed application and/or that region's boundary. For example, displayed menu buttons are associated with one or more amounts of force feedback.

At step 420, a cursor or other indicator is manipulated on the display. For example, user touch, mouse movement, etc., alters position and movement of a cursor on the display.

At step 430, force feedback is provided based on a location of the cursor. For example, if the cursor moves across a boundary from one menu button to another menu button, a force feedback is provided to the user. As another example, a force feedback can be provided with the cursor is within a menu button to help the user identify what the button is.

At step 440, selected functionality is activated. For example, the user can select the menu button over which the cursor is positioned to activate the functionality associated with the menu button.

One or more of the steps of the method 400 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Certain embodiments of the user interface, force feedback, and menu described above may be implemented on a clinical information system, such as the system 500 of FIG. 5. In certain embodiments, an interface including patient information and images may be viewed and/or constructed using a system such as system 500 including at least one data storage 510 and at least one workstation 520. While three workstations 520 are illustrated in system 500, a larger or smaller number of workstations 520 can be used in accordance with embodiments of the presently described technology. In addition, while one data storage 510 is illustrated in system 500, system 500 can include more than one data storage 510. For example, each of a plurality of entities (such as remote data storage facilities, hospitals or clinics) can each include one or more data stores 510 in communication with one or more workstations 520.

As illustrated in system 500, one or more workstations 520 can be in communication with at least one other workstation 520 and/or at least one data storage 510. Workstations 520 can be located in a single physical location or in a plurality of locations. Workstations 520 can be connected to and communicate via one or more networks.

Workstations 520 can be directly attached to one or more data stores 510 and/or communicate with data storage 510 via one or more networks. Each workstation 520 can be implemented using a specialized or general-purpose computer executing a computer program for carrying out the processes described herein. Workstations 520 can be personal computers or host attached terminals, for example. If workstations 520 are personal computers, the processing described herein can be shared by one or more data stores 510 and a workstation 520 by providing an applet to workstation 520, for example.

Workstations 520 include an input device 522, an output device 524 and a storage medium 526. For example, workstations 520 can include a mouse, stylus, microphone and/or keyboard as an input device. Workstations 520 can include a computer monitor, liquid crystal display ("LCD") screen, printer and/or speaker as an output device.

Storage medium 526 of workstations 520 is a computer-readable memory. For example, storage medium 526 can include a computer hard drive, a compact disc ("CD") drive, a USB thumb drive, or any other type of memory capable of storing one or more computer software applications. Storage medium 526 can be included in workstations 520 or physically remote from workstations 520. For example, storage medium 526 can be accessible by workstations 520 through a wired or wireless network connection.

Storage medium 526 includes a set of instructions for a computer. The set of instructions includes one or more routines capable of being run or performed by workstations 520. The set of instructions can be embodied in one or more software applications or in computer code.

Data storage 510 can be implemented using a variety of devices for storing electronic information such as a file transfer protocol ("FTP") server, for example. Data storage 510 includes electronic data. For example, data storage 510 can store patient exam images and/or other information, electronic medical records, patient orders, etc., for a plurality of patients. Data storage 510 may include and/or be in communication with one or more clinical information systems, for example.

Communication between workstations 520, workstations 520 and data storage 510, and/or a plurality of data stores 510 can be via any one or more types of known networks including a local area network ("LAN"), a wide area network ("WAN"), an intranet, or a global network (for example, Internet). Any two of workstations 520 and data stores 510 can be coupled to one another through multiple networks (for example, intranet and Internet) so that not all components of system 500 are required to be coupled to one another through the same network.

Any workstations 520 and/or data stores 510 can be connected to a network or one another in a wired or wireless fashion. In an example embodiment, workstations 520 and data store 510 communicate via the Internet and each workstation 520 executes a user interface application to directly connect to data store 510. In another embodiment, workstation 520 can execute a web browser to contact data store 510. Alternatively, workstation 520 can be implemented using a device programmed primarily for accessing data store 510.

Data storage 510 can be implemented using a server operating in response to a computer program stored in a storage medium accessible by the server. Data storage 510 can operate as a network server (often referred to as a web server) to communicate with workstations 520. Data storage 510 can handle sending and receiving information to and from workstations 520 and can perform associated tasks. Data storage 510 can also include a firewall to prevent unauthorized access and enforce any limitations on authorized access. For instance, an administrator can have access to the entire system and have authority to modify portions of system 500 and a staff member can only have access to view a subset of the data stored at data store 510. In an example embodiment, the administrator has the ability to add new users, delete users and edit user privileges. The firewall can be implemented using conventional hardware and/or software.

Data store 510 can also operate as an application server. Data store 510 can execute one or more application programs to provide access to the data repository located on data store 510. Processing can be shared by data store 510 and workstations 520 by providing an application (for example, a java applet). Alternatively, data store 510 can include a standalone software application for performing a portion of the processing described herein. It is to be understood that separate servers may be used to implement the network server functions and the application server functions. Alternatively, the network server, firewall and the application server can be implemented by a single server executing computer programs to perform the requisite functions.

The storage device located at data storage 510 can be implemented using a variety of devices for storing electronic information such as an FTP server. It is understood that the storage device can be implemented using memory contained in data store 510 or it may be a separate physical device. The storage device can include a variety of information including a data warehouse containing data such as patient medical data, for example.

Data storage 510 can also operate as a database server and coordinate access to application data including data stored on the storage device. Data storage 510 can be physically stored as a single database with access restricted based on user characteristics or it can be physically stored in a variety of databases.

In an embodiment, data storage 510 is configured to store data that is recorded with or associated with a time and/or date stamp. For example, a data entry can be stored in data storage 510 along with a time and/or date at which the data was entered or recorded initially or at data storage 510. The time/date information can be recorded along with the data as, for example, metadata. Alternatively, the time/date information can be recorded in the data in manner similar to the remainder of the data. In another alternative, the time/date information can be stored in a relational database or table and associated with the data via the database or table.

In an embodiment, data storage 510 is configured to store image and/or other medical data for a patient. The medical data can include data such as numbers and text. The medical data can also include information describing medical events. For example, the medical data/events can include a name of a medical test performed on a patient The medical data/events can also include the result(s) of a medical test performed on a patient. For example, the actual numerical result of a medical test can be stored as a result of a medical test. In another example, the result of a medical test can include a finding or analysis by a caregiver that entered as text.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

For example, certain embodiments provide a computer-readable storage medium including a set of instructions for execution on a processing device and associated processing logic. The set of instructions include a user interface routine displaying a plurality of regions representing selectable functionality for an associated plurality of clinical software tools and information. The set of instructions also include a processing routine configured to determine a location and pattern of movement of a cursor movable by a user to select one of the plurality of regions and provide force feedback to the user based on the location and pattern of movement of the cursor to provide a non-visual indication to the user of the location and pattern of movement of the cursor. In certain embodiments, the cursor is movable by a mousing device and wherein the processor provides the force feedback via the mousing device. In certain embodiments, a first click of the mousing device enables force feedback based on the location and pattern of movement of the cursor, and a second click of the mousing device executes functionality corresponding to the region associated with the location of the cursor. In certain embodiments, the cursor is movable by a touchscreen, and the processing routine provides the force feedback via the touchscreen. In certain embodiments, an amount of force feedback varies based on the location of the cursor to distinguish between each of the plurality of regions. In certain embodiments, force feedback allows the user to feel boundaries between the plurality of regions.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, mini-computers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A user interface system providing clinical software tools and information access for a picture archiving and communication system, said user interface system comprising:
 a plurality of regions displayed to represent selectable functionality for an associated plurality of clinical software tools and information, each of said plurality of regions selectable to access functionality including a clinical software tool and information associated with said region;
 a cursor movable by a user to select one of said plurality of regions; and
 a processor configured to determine a location and pattern of movement of said cursor and provide force feedback to said user based on said location and pattern of movement of said cursor to provide a non-visual indication to said user of said location and pattern of movement of said cursor,
 wherein said cursor is movable by a mousing device and wherein said processor provides said force feedback via said mousing device, and wherein a first click of said mousing device activates a force feedback feature to provide force feedback based on said location and pattern of movement of said cursor by the user after activation of the force feedback feature, and wherein a second click of said mousing device executes functionality corresponding to said region associated with said location of said cursor.

2. The user interface of claim 1, wherein said cursor is movable by a touchscreen and wherein said processor provides said force feedback via said touchscreen.

3. The user interface of claim 1, wherein said plurality of regions includes a pie-shaped menu including a plurality of wedge segments each representing a corresponding clinical software tool or information.

4. The user interface of claim 1, wherein an amount of force feedback varies based on said location of said cursor to distinguish between each of said plurality of regions.

5. The user interface of claim 1, wherein said force feedback allows said user to feel boundaries between said plurality of regions.

6. The user interface of claim 5, wherein user selection after moving said cursor across a boundary into a region expands that region.

7. The user interface of claim 1, wherein a degree of force applied by said user determines functionality activated in a region.

8. A method for providing force feedback to a user in conjunction with a user interface or application display in a clinical system, said method comprising:

associating a degree of force feedback with a region of a display and a boundary of the region, the display providing a plurality of regions displayed to represent selectable functionality for an associated plurality of clinical software tools and information, each of said plurality of regions selectable to access functionality including a clinical software tool and information associated with said region;

tracking manipulation of a cursor with respect to the region on the display to determine a location and pattern of movement of said cursor, said cursor movable by a user via a mousing device to select one of said plurality of regions;

providing said force feedback to a user via said mousing device when said cursor enters and leaves said region based on a first click of said mousing device to provide a non-visual indication to said user of said location and pattern of movement of said cursor, said first click to activate a force feedback feature to provide said force feedback after activation of the force feedback feature; and executing functionality corresponding to said region based on a second click of said mousing device.

9. The method of claim 8, wherein an amount of force feedback varies based on said location of said cursor to distinguish between each of a plurality of regions.

10. The method of claim 8, wherein said force feedback allows said user to feel a boundaries surrounding said region.

11. The method of claim 8, wherein user selection after moving said cursor across said boundary into said region expands said region.

12. A computer-readable storage medium including a set of instructions for execution on a processing device and associated processing logic, the set of instructions comprising:

a user interface routine displaying a plurality of regions representing selectable functionality for an associated plurality of clinical software tools and information, each of said plurality of regions selectable to access functionality including a clinical software tool and information associated with said region; and a processing routine configured to determine a location and pattern of movement of a cursor movable by a user to select one of said plurality of regions and to provide force feedback to said user based on said location and pattern of movement of said cursor to provide a non-visual indication to said user of said location and pattern of movement of said cursor, wherein said cursor is movable by a mousing device and wherein said processing routine is configured to provide force feedback to said user via said mousing device based on said location and pattern of movement of said cursor based on a first click of said mousing device, said first click to activate a force feedback feature to provide said force feedback after activation of the force feedback feature, and to execute functionality corresponding to said region associated with said cursor based on a second click of said mousing device.

13. The computer-readable storage medium of claim 12, wherein said cursor is movable by a touchscreen and wherein said processing routine provides said force feedback via said touchscreen.

14. The computer-readable storage medium of claim 12, wherein an amount of force feedback varies based on said location of said cursor to distinguish between each of said plurality of regions.

15. The computer-readable storage medium of claim 12, wherein said force feedback allows said user to feel boundaries between said plurality of regions.

* * * * *